(12) United States Patent
Larma et al.

(10) Patent No.: US 6,531,458 B1
(45) Date of Patent: Mar. 11, 2003

(54) STABLE COMPOSITIONS COMPRISING LEVOSIMENDAN AND ALGINIC ACID

(75) Inventors: Ilkka Larma, Springfield, NJ (US); Maarit Bäckman, Helsinki (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/673,793

(22) PCT Filed: Apr. 23, 1999

(86) PCT No.: PCT/FI99/00331

§ 371 (c)(1),
(2), (4) Date: Dec. 6, 2000

(87) PCT Pub. No.: WO99/55337

PCT Pub. Date: Nov. 4, 1999

(30) Foreign Application Priority Data

Apr. 23, 1998 (FI) .................................................. 980902

(51) Int. Cl.⁷ ........................ A01N 43/04; A61K 31/715
(52) U.S. Cl. .......................................... 514/54; 514/247
(58) Field of Search ................... 514/247, 54; 544/239; 424/464, 490, 434, 449, 402, 484

(56) References Cited

U.S. PATENT DOCUMENTS

| | | | |
|---|---|---|---|
| 4,079,125 A | 3/1978 | Sipos | |
| 4,716,042 A | 12/1987 | Blank | ......................... 424/474 |
| 4,906,630 A | * 3/1990 | Studt et al. | .................. 514/218 |

FOREIGN PATENT DOCUMENTS

| | | |
|---|---|---|
| EP | 0 091 767 | 10/1983 |
| EP | 0 123 291 | 10/1984 |
| EP | 0 383 449 | 8/1990 |
| WO | WO 92/12135 | 7/1992 |
| WO | WO 93/21921 | 11/1993 |
| WO | WO 98/01111 | 1/1998 |
| WO | WO 99/16443 | 4/1999 |

OTHER PUBLICATIONS

Sandell et al., "Pharmacokinetics of Levosimendan in Healthy Volunteers and Patients with Congestive Heart Failure," J. Cardiovascular Pharmacology, vol. 26, Suppl. 1, pp. S57–S62 (1995).

Sundberg et al., "Hemodynamic and Neurohumoral Effects of Levosimendan, a New Calcium Sensitizer, at Rest and During Exercise in Healthy Men," American Journal of Cardiology, vol. 75, pp. 1061–1066 (1995).

* cited by examiner

*Primary Examiner*—James O. Wilson
*Assistant Examiner*—Ganapathy Krishnan
(74) *Attorney, Agent, or Firm*—Finnegan, Henderson, Farabow, Garrett & Dunner, L.L.P.

(57) ABSTRACT

The present invention relates to pharmaceutical compositions of levosimendan comprising alginic acid for improving the stability of levosimendan in the compositions. Levosimendan is useful in the treatment of congestive heart failure.

9 Claims, No Drawings

STABLE COMPOSITIONS COMPRISING LEVOSIMENDAN AND ALGINIC ACID

This application is a national stage filing of PCT International Application No. PCT/FI99/00331, filed on Apr. 23, 1999, which published in English.

TECHNICAL FIELD

The present invention relates to pharmaceutical compositions, particularly for oral administration, with improved stability comprising levosimendan, the (−) enantiomer of [[4-(1,4,5,6-tetrahydro-4-methyl-6-oxo-3-pyridazinyl)phenyl]-hydrazono]propanedinitrile, as the active ingredient. Levosimendan is useful in the treatment of congestive heart failure.

BACKGROUND OF THE INVENTION

Levosimendan, which is the (−)-enantiomer of [[4-(1,4,5,6-tetrahydro-4-methyl-6-oxo-3-pyridazinyl)phenyl] hydrazono]propanedinitrile, and the method for its preparation is described in EP 565546 B 1. Levosimendan is potent in the treatment of heart failure and has significant calcium dependent binding to troponin. Levosimendan is represented by the formula:

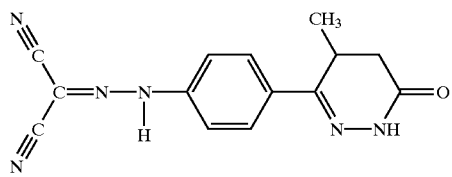

The hemodynamic effects of levosimendan in man are described in Sundberg, S. et al., Am. J. Cardiol., 1995; 75: 1061–1066. Pharmacokinetics of levosimendan in man after i.v. and oral dosing is described in Sandell, E.-P. et al., J. Cardiovasc. Pharmacol., 26(Suppl.1), S57–S62, 1995. The use of levosimendan in the treatment of myocardial ischemia is described in WO 93/21921. Clinical studies have confirmed the beneficial effects of levosimendan in heart failure patients.

The preparation of pharmaceutical compositions of levosimendan, particularly for oral use, has proved to be difficult. When combined with conventional excipients levosimendan shows poor stability and easily degrades under storage conditions. Therefore, there is a need for pharmaceutical preparations of levosimendan which show improved stability of the active ingredient under storage.

SUMMARY OF THE INVENTION

It has now been unexpectedly found that alginic acid significantly improves the stability of levosimendan in pharmaceutical compositions.

Thus the present invention provides a pharmaceutical composition of levosimendan, particularly for oral administration, with improved stability comprising alginic acid as a stability improving agent.

DETAILED DESCRIPTION

The compositions of the invention comprise generally about 0.1–99 % of alginic acid per weight of the composition. More typically, a composition of the invention comprises about 5–70 %, preferably about 10–40 %, of alginic acid per weight of the composition.

Typically, the composition of the invention is for oral administration. Such compositions include solid compositions in the form of e.g. tablets, dragees, capsules, powders and granules. The contents of the active compound in the composition of the invention is generally from about 0.01 to 100%, preferably from 0.1 to 20%, most preferably from 0.5 to 10% per weight. In general levosimendan is administered orally to man in doses from about 0.1 to 10 mg, preferably from 0.5 to 5 mg once or several times a day depending on the age, body weight and condition of the patient.

In addition to levosimendan and alginic acid the composition of the invention may comprise pharmaceutically acceptable carriers and excipients. Pharmaceutically acceptable carriers and excipients include those which are used according to standard pharmaceutical practice and which are compatible with the active ingredient. For oral administration in tablet form, suitable carriers and excipients include microcrystalline cellulose such as Avicel PH101, lactose, corn starch, magnesium stearate, stearic acid, calcium phosphate and talc. For oral administration in capsule form, useful carriers and excipients include micro-crystalline cellulose, lactose, corn starch, magnesium stearate, stearic acid and talc. Capsules can be prepared by mixing the active ingredient with the carriers and excipients and placing the powdery mixture in capsules, e.g. hard gelatine capsules. Tablets can be prepared by mixing the active ingredient with the carriers and excipients and compressing the powdery mixture into tablets.

The composition may be designed to release the active ingredient rapidly or in a controlled/extended fashion. Typically long-acting compositions are prepared by mixing the drug, a release controlling agent and possible excipients, and pressing the mixture into matrix tablets, or by coating a core of active ingredient with a release controlling coating so as to obtain coated tablets or granules. Typical release controlling agents include hydrophilic gel forming polymers such as hydroxypropylmethyl cellulose, which is commercially available in various types, e.g. Methocel K100LV (m.w. 26,000 g/mol), Methocel K4M (m.w. 86,000 g/mol, Methocel K15M (m.w. 120,000 g/mol) and Methocel K100M. The viscosity of these grades in 2% water solution (20° C.) is 100 cP, 4000 cP, 15000 cP and 100000 cP, respectively.

The following examples are meant to further illustrate the invention without limitation.

EXAMPLE 1. The stability of formulations of the invention (1 and 2) and reference formulations (1–4) are compared in storage conditions.

Formulation 1 (hard gelatine capsule):

| | |
|---|---|
| Levosimendan | 2 mg |
| Methocel K100LV | 46 mg |
| Alginic acid | 23 mg |
| Avicel PH101 | 69.5 mg |
| Stearic acid | 1.5 mg |

Formulation 2 (pressed tablet): Levosimendan : alginic acid 1:10

Reference formulation 1 (hard gelatine capsule):

| | |
|---|---|
| Levosimendan | 2 mg |
| Methocel K4M | 35 mg |

-continued

| Avicel PH101 | 101.6 mg |
|---|---|
| Stearic acid | 1.4 mg |

Reference formulation 2 (hard gelatine capsule):

| Levosimendan | 2 mg |
|---|---|
| Lactose | 197 mg |
| Magnesium stearate | 1 mg |

Reference formulation 3 (pressed tablet): Levosimendan : lactose 1:100

Reference formulation 4 (pressed tablet): Levosimendan: magnesium stearate 1:1

Formulation 1, consisting of a granule portion and a powder portion, was prepared by mixing Methocel K100LV, alginic acid and levosimendan (1 mg) until homogenous in a suitable mixer such as Turbula mixer or Zanchetta container mixer. The mass was dry granulated by slugging (compressed using a tabletting machine). The compacted mass was sieved and granules of 0.7–1.7 mm were collected. For the powder portion, Avicel PH101 and levosimendan (1 mg) was sieved and mixed until homogenous in a suitable mixer such as Turbula mixer or Zanchetta container mixer. The granule portion and the powder portion and the stearic acid were mixed until homogenous in a suitable mixer such as Turbula mixer or Zanchetta container mixer. The mass was filled into hard gelatine capsules no 3.

In Reference formulations 1 and 2 the material was in a powder form. These formulations were prepared by mixing the components until homogenous in a suitable mixer such as Turbula mixer or Zanchetta container mixer. The mass was then filled into hard gelatine capsules no 3.

Formulation 2 and Reference formulations 3 and 4 were prepared by mixing the components until homogenous in a suitable mixer such as Turbula mixer or Zanchetta container mixer. The mixture was then pressed into tablets using a conventional tabletting machine.

The stability of the formulations in storage conditions was assessed by determining the level of degradation products of levosimendan in the formulations after storage. The results are given in Table 1.

TABLE 1

The presence of levosimendan degradation products (OR-1420 and OR-1368) in formulations of the invention (1–2) and in reference formulations (1–4) after storage.
Rh = relative humidity.

| | Storage conditions | OR-1420 formed | OR-1368 formed | Number of unknown degradation products |
|---|---|---|---|---|
| Formulation 1 | 9 months 2–8° C. | 0 | 0 | 0 |
| Formulation 2 | 8 months 25° C., rh 60% | 0 | 0 | 0 |
| Ref. formulation 1 | 9 months 2–8° C. | 0.25% | 0.25% | 1, 0.05% |
| Ref. formulation 2 | 3 months 25° C., rh 60% | 1.32% | 0.07% | 5, 0.54% |
| Ref. formulation 3 | 3 months 25° C., rh 60% | 0.75% | 0.23% | 10, 0.93% |
| Ref. formulation 4 | 7 weeks 25° C. | 0 | 0 | 1, 1.0% |

Table 1 shows that alginic acid significantly improved the stability of levosimendan formulations in storage conditions as demonstrated by the absence of any degradation products of levosimendan after 8–9 months of storage. In contrast, the reference formulations containing no alginic acid show significant formation of levosimendan degradation products.

What is claimed is:

1. A pharmaceutical composition comprising levosimendan and alginic acid.
2. A composition of claim 1, wherein the amount of alginic acid is 0.1–99% by weight of the composition.
3. A composition of claim 2, wherein the amount of alginic acid is 5–70% by weight of the composition.
4. A composition of claim 1, wherein the composition is for oral administration.
5. A composition of claim 4, which is in the form of tablets, dragees, capsules, powders or granules.
6. A composition of claim 1, wherein the amount of levosimenden in the composition is from 0.1 to 20% by weight of the composition.
7. A composition of claim 1, wherein the amount of levosimenden is 0.1 to 10 mg.
8. A composition of claim 2, wherein the amount of alginic acid is 10–40% by weight of the composition.
9. A method for improving the stability of levosimenden in a pharmaceutical composition, which comprises adding to the composition an effective amount of alginic acid as a stability improving agent.

\* \* \* \* \*